United States Patent
Hsieh et al.

(10) Patent No.: US 8,124,128 B2
(45) Date of Patent: Feb. 28, 2012

(54) AMPHIPHILIC BLOCK COPOLYMERS AND NANO PARTICLES COMPRISING THE SAME

(75) Inventors: Ming-Fa Hsieh, Hsinchu (TW); Hsuen-Tseng Chang, Kaohsiung (TW); Chin-Fu Chen, Taipei County (TW); Yuan-Chia Chang, Taipei (TW); Pei Kan, Hsinchu (TW); Tsai-Yu Lin, Changhua County (TW); Yuan-Hung Hsu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 550 days.

(21) Appl. No.: 11/268,544

(22) Filed: Nov. 8, 2005

(65) Prior Publication Data

US 2007/0104654 A1     May 10, 2007

(51) Int. Cl.
 *A61K 48/00* (2006.01)
 *A61K 9/14* (2006.01)
 *A61K 31/4745* (2006.01)
 *C08G 63/91* (2006.01)
 *C08G 63/48* (2006.01)

(52) U.S. Cl. .......... 424/489; 424/46; 514/283; 525/437; 525/54.2; 977/906; 977/926

(58) Field of Classification Search .................. 424/489
See application file for complete search history.

(56) References Cited

U.S. PATENT DOCUMENTS 5,543,158 A    8/1996   Gref et al.
(Continued)

FOREIGN PATENT DOCUMENTS

WO      WO03/074026     *    9/2003
(Continued)

OTHER PUBLICATIONS

Gao et al. Characterization of the antitumor-promoting activity of camptothecin in SENCAR mouse skin, "Carcinogenesis," vol. 17, No. 5, pp. 1141-1148, 1996, Accessed Jun. 17, 2008.*

(Continued)

*Primary Examiner* — Richard Schnizer
*Assistant Examiner* — Audrea Buckley
(74) *Attorney, Agent, or Firm* — Occhiuti Rohlicek & Tsao LLP (57) ABSTRACT

An amphiphilic block copolymer. The amphiphilic block copolymer includes one or more hydrophilic polymers, one or more hydrophobic polymer, and one or more zwitterions. The invention also provides a nano particle and carrier comprising the amhpiphilic block copolymer for delivery of water-insoluble drugs, growth factors, genes, or cosmetic substances.

19 Claims, 6 Drawing Sheets

U.S. PATENT DOCUMENTS

| | | | |
|---|---|---|---|
| 5,741,852 | A | 4/1998 | Marchant et al. |
| 6,007,845 | A | 12/1999 | Domb et al. |
| 6,201,072 | B1 * | 3/2001 | Rathi et al. .................... 525/415 |
| 6,204,324 | B1 | 3/2001 | Shuto et al. |
| 6,322,805 | B1 | 11/2001 | Kim et al. |
| 2006/0183863 | A1 * | 8/2006 | Huang et al. .................. 525/234 |

FOREIGN PATENT DOCUMENTS

| WO | WO2004021976 | 3/2004 |
|---|---|---|

OTHER PUBLICATIONS

Jeong et al., International Journal of Pharmaceutics 188 (1999) 49-58.

Arasawa et al.; "Gratfing of Zwitterion-Type Polymers onto Silica Gel Surface and their Properties"; Reactive and Functional Polymers; 61:153-161 (2004).

Yuan and Armes; "Synthesis of Biocompatible Poly[2-(methacryloyloxy)ethyl phosphorylcholine]-Coated Magnetite Nanoparticles"; Langmuir; 22:10989-10993 (2006).

Yuan et al.; "Chemical Graft Polymerization of Sulfobetaine Monomer on Polyurethane Surface for Reduction in Platelet Adhesion"; Colloids and Surfaces B: Biointerfaces; 39:87-94 (2004).

Nederberg et al.; "Phosphoryl Choline Introduces Dual Activity in Biomimetic Ionomers"; J.AM. Chem. Soc.; 126:15350-15351 (2004).

Jiang et al.; "Platelet Adhesive Resistance of Polyurethane Surface Grafted with Zwitterions of Sulfobetaine"; Colloids and Surfaces B: Biointerfaces; 36:19-26 (2004).

Chen et al.; "Polymeric Phosphorycloline-Camptothecin Conjugates Prepared by Controlled Free Radical Polymerization and Click Chemistry"; Bioconjugate Chem.; 20:2331-2341 (2009).

Konno et al.; "Preparation of Nanoparticles Composed with Bioinspired 2-methacryloyloxyethyl Phosphorylcholine Polymer" Biomaterials; 22:1883-1889 (2001).

Flores et al.; "Reversible "Self-Locked" Micelles from a Zwitterion-Containing Triblock Copolymer"; Macromolecules; 42:4941-4945 (2009).

Meng et al.; "Phosphorylcholine Modified Chitosan: Appetent and Safe Material for Cells"; Carbohydrate Polymers; 70:82-88 (2007).

Yung and Cooper; "Neutrophil Adhesion on Phosphorylcholine-Containing Polyurethanes"; Biomaterials; 19:31-40 (1998).

Chan et al.; "Approaches to Improving the Biocompatibility of Porous Perfluoropolyethers for Ophthalmic Applications"; Biomaterials; 27:1287-1295 (2006).

Jiang et al.; "Blood Compatibility of Polyurethane Surface Grafted Copolymerization with Sulfobetaine Monomer"; Colloids and Surfaces B: Biointerfaces; 36:27-33 (2004).

Nederberg et al.; "Synthesis, Characterization, and Properties of Phosphoryl Choline Functionalized Poly €-Caprolactone and Charged Phospholipid Analogues"; Macromolecules; 37:954-965 (2004).

* cited by examiner

AMPHIPHILIC BLOCK COPOLYMERS AND NANO PARTICLES COMPRISING THE SAME

BACKGROUND

The invention relates to a polymer, and more specifically to a bio-compatible and bio-degradable block copolymer and a nano particle comprising the same.

To improve curative effects and reduce side effects, an optimal drug delivery carrier which can precisely target at tumor cell and produce high drug concentration around the focus is required. Such carrier materials must be bio-compatible, bio-degradable, and be invisible to immune system detection to avoid macrophage attack. Common carrier materials comprise block copolymers. Some, however, lack bio-degradability, long-term stability, and invisibility to the immune cells in blood circulation.

Sugiyama provides a zwitterionic copolymer comprising a hydrophilic chain of 2-(methacryloyloxy)ethyl phosphorylcholine (MPC) and a hydrophobic chain ends of cholesteryl with critical micelle concentration (CMC) of $2.5 \times 10^{-4}$–$2.7 \times 10^{-5}$ wt % recited in Journal of Polymer Science Part A: Polymer Chemistry (2003) 1992-2000. Such material forms a complex with cholesterol molecules in condensed layer morphology with a 3.52 nm interval therebetween. This copolymer provides hemo-compatibility and encapsulates water-insoluble drugs by hydrophobic cholesterol groups attached on the polymer chains. The material, however, lacks bio-degradability.

Stenzel provides a zwitterionic block copolymer comprising poly(2-acryloyloxyethyl phosphorylcholine) and poly(butyl acrylate) with bio-compatibility formed by reversible addition fragmentation transfer (RAFT) recited in Macromolecular Bioscience (2004) 445-453. The nano particle formed in water and methanol binary solvent thereby has a diameter of about 100-180 nm. This copolymer, however, also lacks bio-degradability.

Nakabayashi provides a bio-degradable poly(L-lactic acid) (PLLA) material comprising phosphorylcholine such as L-α-glycerophosphorylcholine (LGPC) recited in Journal of Biomedical Materials Research part A (2003) 164-169. Various molecular weight PLLA materials can be polymerized using LGPC as an initiator. According to a blood cell experiment, as the phosphorylcholine content of PLLA increases, blood-cell adsorption reduces. This material, however, lacks micelle characteristics.

Oishi provides a novel zwitterionic poly(fumaramate) material comprising phosphorylcholine with CMC of about $1.7 \times 10^{-3}$–$1.0 \times 10^{-3}$ M recited in Polymer (1997) 3109-3115. The CMC is altered by conducting isopropyl and methyl groups to fumaramate. According to a bovine serum albumin adsorption experiment, as the phosphorylcholine content of poly(fumaramate) increases, bovine serum albumin adsorption is reduced.

Sommerdijk provides a polystyrene material comprising tetra(ethylene glycol) and phosphorylcholine bonded to its side chain with bio-compatibility recited in Journal of Polymer Science Part A: Polymer Chemistry (2001) 468-474. According protein adsorption experiment and in-vitro human dermal fibroblasts culture, only polystyrene material containing tetra(ethylene glycol) and phosphorylcholine can reduce protein adsorption and fibroblasts growth, as compared with polystyrene bonded with tetra(ethylene glycol) or phosphorylcholine alone.

Langer provides a bio-degradable injection-type nano particle comprising diblock (AB) or triblock (ABC) copolymer disclosed in U.S. Pat. Nos. 5,543,158 and 6,007,845. A is a hydrophilic chain such as poly(alkylene glycol), B is a hydrophobic chain such as PLGA, and C is a bio-active substance such as antibody. The particle can target at cells or organs by the bio-active substance bonded thereto. These applications, however, fail to disclose AB or ABC can provide invisibility to bio-recognition.

Kim provides a bio-degradable drug-contained micelle comprising diblock (BA) or triblock (ABA or BAB) copolymer with a preferable molecular weight of about 1430-6000 and a hydrophilic chain ratio of 50-70 wt % disclosed in U.S. Pat. No. 6,322,805. A is a bio-degradable hydrophobic chain and B is a hydrophilic chain such as PEG. Drugs such as paclitaxel are encapsulated by physical manner. The application, however, fails to disclose ABC-type triblock copolymer.

Marchant provides an anti-thrombosis triblock copolymer comprising a hydrophobic bio-degradable polymer and a hydrophilic polysaccharide chain such as dextran or heparin disclosed in U.S. Pat. No. 5,741,852.

Ishihara provides a method for preparing a phosphorylcholine-contained polymer in aqueous phase disclosed in U.S. Pat. No. 6,204,324. Polymerizable monomers, phosphorylcholine, are polymerized by adding initiator in aqueous medium. The results are then purified by a separation film, containing impurity less than 2000 ppm.

SUMMARY

The invention provides a block copolymer comprising one or more hydrophobic blocks and one or more zwitterions. The block copolymer further comprises one or more hydrophilic blocks bonded to the hydrophobic block.

The invention also provides a nano particle comprising one or more the disclosed block copolymers.

The invention further provides a nano carrier comprising the disclosed nano particle and an active substance encapsulated inside the particle.

A detailed description is given in the following embodiments with reference to the accompanying drawings.

BRIEF DESCRIPTION OF THE DRAWINGS

Embodiments of the invention can be more fully understood by reading the subsequent detailed description and examples with references made to the accompanying drawings, wherein.

DETAILED DESCRIPTION

The invention provides a block copolymer comprising one or more hydrophobic polymers and one or more zwitterions.

The copolymer is an amphiphilic block copolymer. The block copolymer comprises diblock copolymer, with CMC of about 0.1-0.01 wt %. The hydrophobic block has a molecular weight of about 1000-30000 and may comprise polyester such as polycaprolactone (PCL), polyvalerolactone (PVL), poly(lactide-co-glycolide) (PLGA), polylactic acid (PLA), polybutyrolactone (PBL), polyglycolide, and polypropiolactone (PPL). The zwitterions may comprise phosphorylcholine (PC), sulfobetaine (NS), or amino acids.

The block copolymer further comprises one or more hydrophilic blocks bonded to the hydrophobic block to form a triblock copolymer of hydrophilic block-hydrophobic block-zwitterion. The hydrophilic block has a molecular weight of about 550-20000 and may comprise polyethylene glycol (PEG), hyaluronic acid (HA), or poly-γ-glutamic acid (γ-PGA). The block copolymer comprising diblock or triblock is bio-degradable and bio-compatible.

The invention also provides a nano particle comprising one or more the disclosed block copolymers.

The nano particle has a hydrophobic interior and hydrophilic surface and its diameter is about 20-1000 nm.

Due to the chain flexibility of hydrophilic block in blood, zwitterions capable of keeping particle structure without recognized by immune cells during drug releasing period, and a hydrophobic block decomposable by enzyme or hydrolysis, the novel biomedical nano particle provides bio-compatibility, bio-degradability, and invisibility to immune cells. After the hydrophobic block is decomposed, remaining harmless substances such as hydrophilic block and zwitterion are dissolved in blood and then removed from renal system.

The invention further provides a nano carrier comprising the disclosed nano particle and an active substance encapsulated inside the particle.

The active substance may comprise water-insoluble drugs such as camptothecin or derivatives thereof, growth factors, genes, or water-insoluble cosmetic substances such as ingredients for skincare. The nano carrier can be delivered by oral, transdermal administration, injection, or inhalation.

The preparation of the biomedical polymer is described as follows. First, a copolymer comprising a hydrophilic block and a hydrophobic block, such as PEG-PCL, PEG-PVL, and PEG-PPL, is prepared. Next, the copolymer is dissolved in a solvent, such as dichloromethane ($CH_2Cl_2$), and its terminal is added with a chemical group, such as 2-chloro-2-oxo-1,3,2-dioxaphospholane (COP), succinic anhydride (SA), and 3-(dimethylamino)propylamine (DMAPA), to form a modified copolymer. After the modified copolymer is dissolved in a solvent such as acetonitrile and chloroform, its modified terminal is reacted with another chemical group, such as trimethylamine (TMA), 1,3-propane sultone (PS), and benzyl histidine, to form zwitterions. Thus, a copolymer comprising a hydrophilic block, a hydrophobic block, and zwitterions is obtained.

EXAMPLES

Synthesis of PEG-PCL-PC (1) Polymerization of PEG-PCL:

60 g poly(ethylene glycol) (PEG, 5000 g/mole) and 12 g ε-caprolactone were added to a 250 ml glass reactor (8 cm×8 cm×10 cm) with gradual heating until totally dissolved. The PEG-PCL polymerization then began by adding 0.38 ml catalyst of stannous 2-ethylhexanoate at 160° C. for 24 hours. The crude product was purified by dissolving in dichloromethane and re-precipitating in diethyl ether. The purification was repeated three times and vacuum-dried at 40° C. for 24 hours. Thus, a PEG-PCL copolymer was obtained.

(2) Synthesis of PEG-PCL-COP:

5 g PEG-PCL copolymer and 0.43 g triethylamine (TEA) were dissolved in 70 ml dichloromethane at 0° C. with mechanical stirring in a 250 ml flask. Another solution containing 3.5 g 2-chloro-2-oxo-1,3,2-dioxaphospholane (COP) dissolved in 30 ml dichloromethane was prepared simultaneously. The COP-contained solution was then gradually dropped into the flask within 1 hour and reacted at 0° C. for 4 hours. The resulting solution was then warmed to room temperature and filtered by 0.45 μm filter paper to remove the by-product, triethylammonium chloride. After removing dichloromethane, a modified copolymer, PEG-PCL-COP, was obtained.

Figure 1:
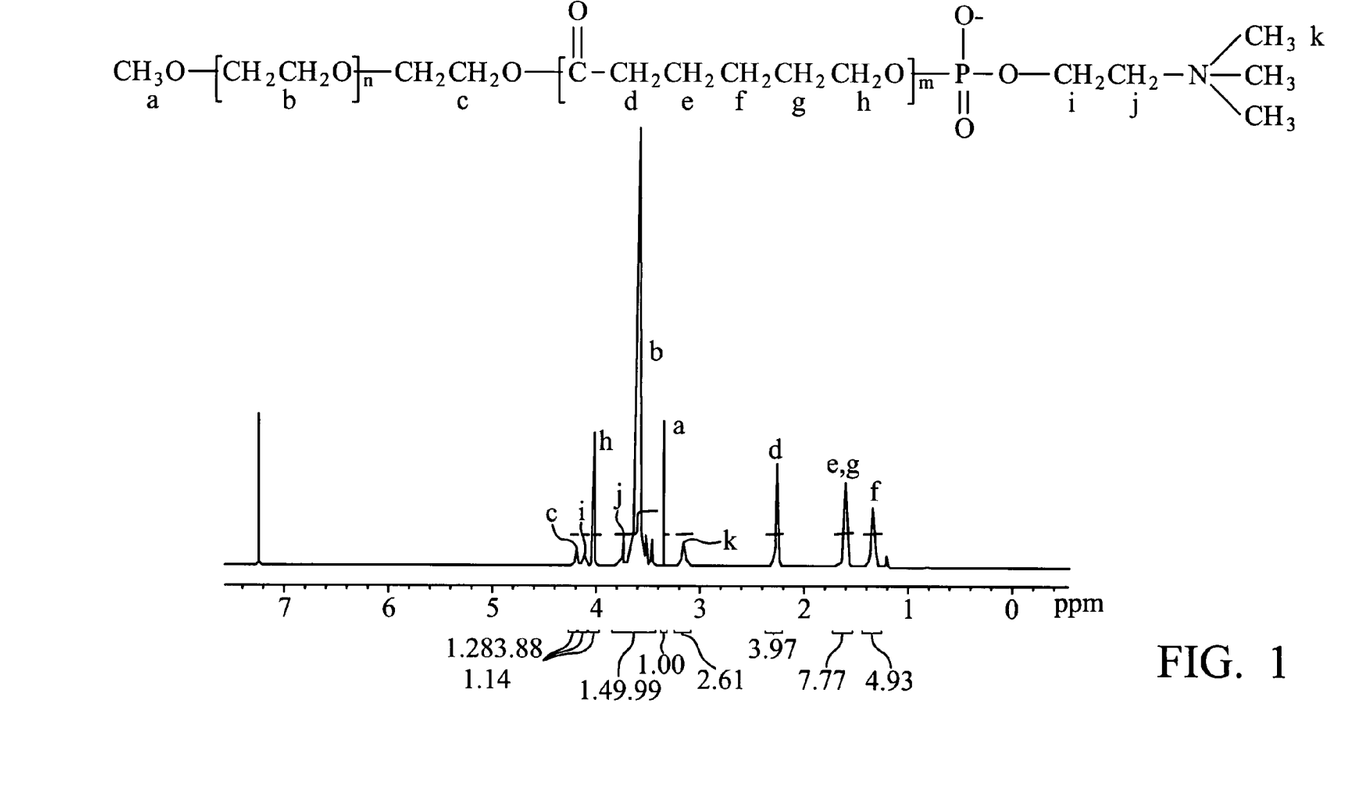
FIG. 1 shows $^1$H-NMR spectrum of PEG-PCL-PC.

(3) Synthesis of PEG-PCL-PC:

PEG-PCL-COP was dissolved in 70 ml acetonitrile at room temperature in a flask. 10 ml trimethylamine (33% in ethanol) was then dropped into the flask and reacted at 60° C. for 24 hours with stirring. After removing the solvent, the resulting solution was extracted three times by dichloromethane/water. After removing dichloromethane and vacuum-drying for 24 hours, white solid resulted, PEG-PCL-PC copolymer, were obtained. Its $^1$H-NMR is shown in FIG. 1.

Synthesis of PEG-PVL-PC (1) Polymerization of PEG-PVL:

60 g poly(ethylene glycol) (PEG, 5000 g/mole) and 12 g δ-valerolactone were added to a 250 ml glass reactor (8 cm×8 cm×10 cm) with gradual heating until totally dissolved. The PEG-PVL polymerization then began by adding 0.38 ml catalyst of stannous 2-ethylhexanoate at 160° C. for 8 hours. The result was dissolved in dichloromethane and re-precipitated by adding diethyl ether. The white precipitate was then washed three times and vacuum-dried at 40° C. for 24 hours. Thus, a PEG-PVL copolymer was obtained.

(2) Synthesis of PEG-PVL-COP:

5 g PEG-PVL copolymer and 0.43 g triethylamine (TEA) were dissolved in 70 ml dichloromethane at 0° C. with mechanical stirring in a 250 ml flask. Another solution containing 3.5 g 2-chloro-2-oxo-1,3,2-dioxaphospholane (COP) dissolved in 30 ml dichloromethane was prepared simultaneously. The COP-contained solution was then gradually dropped into the flask within 1 hour and reacted at 0° C. for 6 hours. The resulting solution was then warmed to room temperature and filtered by 0.45 μm filter paper to remove the by-product, triethylammonium chloride. After removing dichloromethane, a modified copolymer, PEG-PVL-COP, was obtained.

(3) Synthesis of PEG-PVL-PC:

PEG-PVL-COP was dissolved in 70 ml acetonitrile at room temperature in a flask. 10 ml trimethylamine (33% in ethanol) was then dropped into the flask and reacted at 60° C. for 24 hours with stirring. After removing the solvent, the resulting solution was extracted three times by dichloromethane/water. After removing dichloromethane and vacuum-drying for 24 hours, white solid results, PEG-PVL-PC copolymer, were obtained.

Synthesis of PEG-PCL-NS (1) Synthesis of PEG-PCL-SA:

3 g PEG-PCL copolymer and 0.1 g 4-dimethylaminopyridine (DMAP) were dissolved in 60 ml dichloromethane at 0° C. with mechanical stirring in a 250 ml flask. Another solution containing 0.1 g triethylamine (TEA) and 0.5 g succinic anhydride (SA) dissolved in 10 ml dichloromethane was prepared simultaneously. The SA-contained solution was then gradually dropped into the flask within 1 hour and reacted at 25° C. for 24 hours. The resulting solution was then precipitated three times by adding diethyl ether and vacuum-dried for 24 hours. Thus, a modified copolymer, PEG-PCL-SA, was obtained.

(2) Synthesis of PEG-PCL-TA:

2 g PEG-PCL-SA copolymer, 0.2 g 1,3-dicyclohexylcarbodiimide (DCC), and 0.1 g N-hydroxysuccinimide (NHS) were dissolved in 40 ml dichloromethane at 0° C. with mechanical stirring in a 250 ml flask. Another solution containing 0.1 g 3-(dimethylamino)propylamine (DMAPA) dissolved in 10 ml dichloromethane was prepared simultaneously. The DMAPA-contained solution was then gradually dropped into the flask within 1 hour and reacted at 25° C. for 24 hours. The resulting solution was then precipitated three times by adding diethyl ether and vacuum-dried for 24 hours. Thus, a modified copolymer, PEG-PCL-TA, was obtained.

Figure 2:
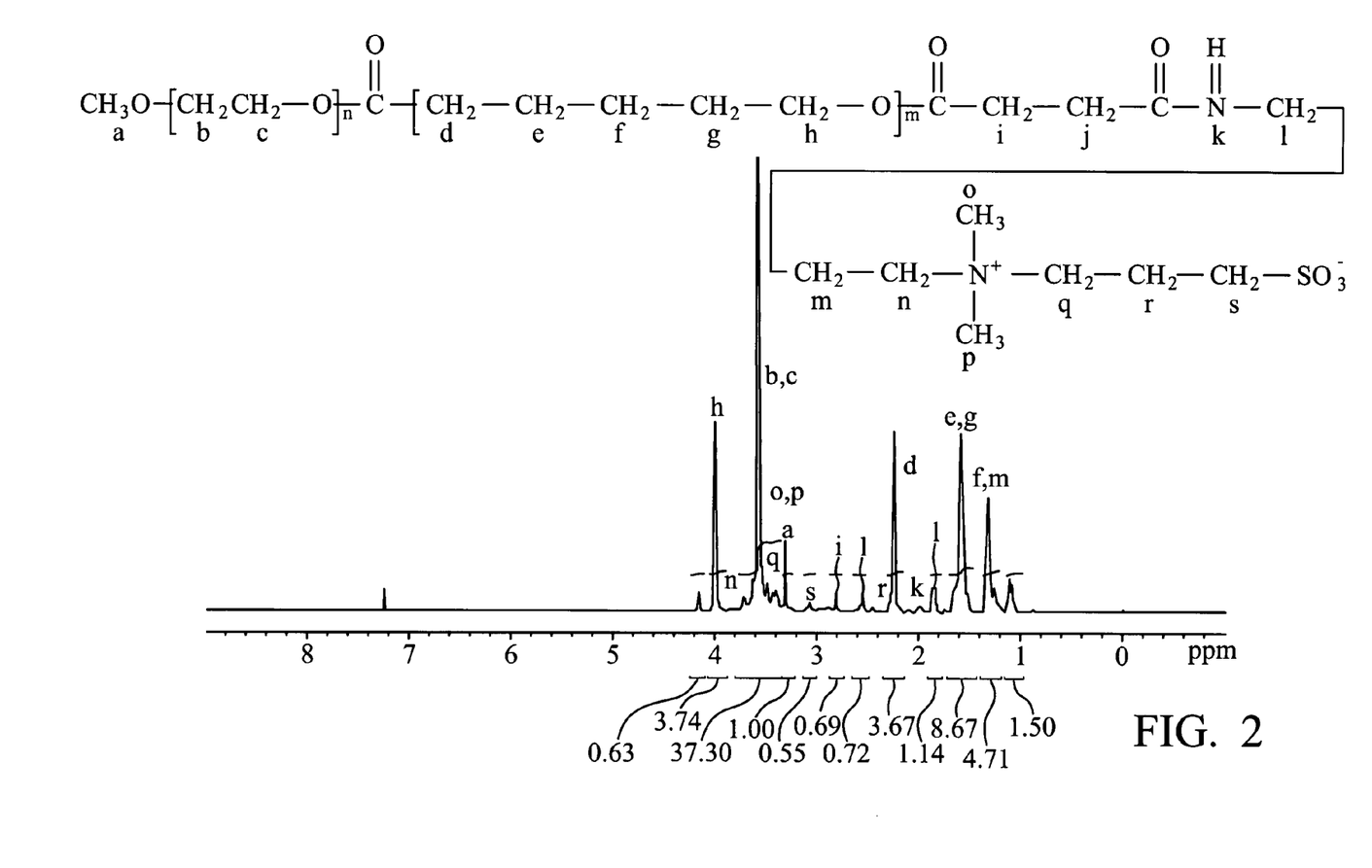
FIG. 2 shows $^1$H-NMR spectrum of PEG-PCL-NS.

(3) Synthesis of PEG-PCL-NS:

0.15 g PEG-PCL-TA was dissolved in 60 ml chloroform at 0° C. in a flask. 0.36 g 1,3-propane sultone (20% in chloroform) was then dropped into the flask and reacted at 30° C. for 24 hours with stirring. The resulting solution was then precipitated three times by adding diethyl ether and vacuum-dried for 24 hours. Thus, a copolymer, PEG-PCL-NS, was obtained. Its $^1$H-NMR is shown in FIG. 2.

Figure 3:
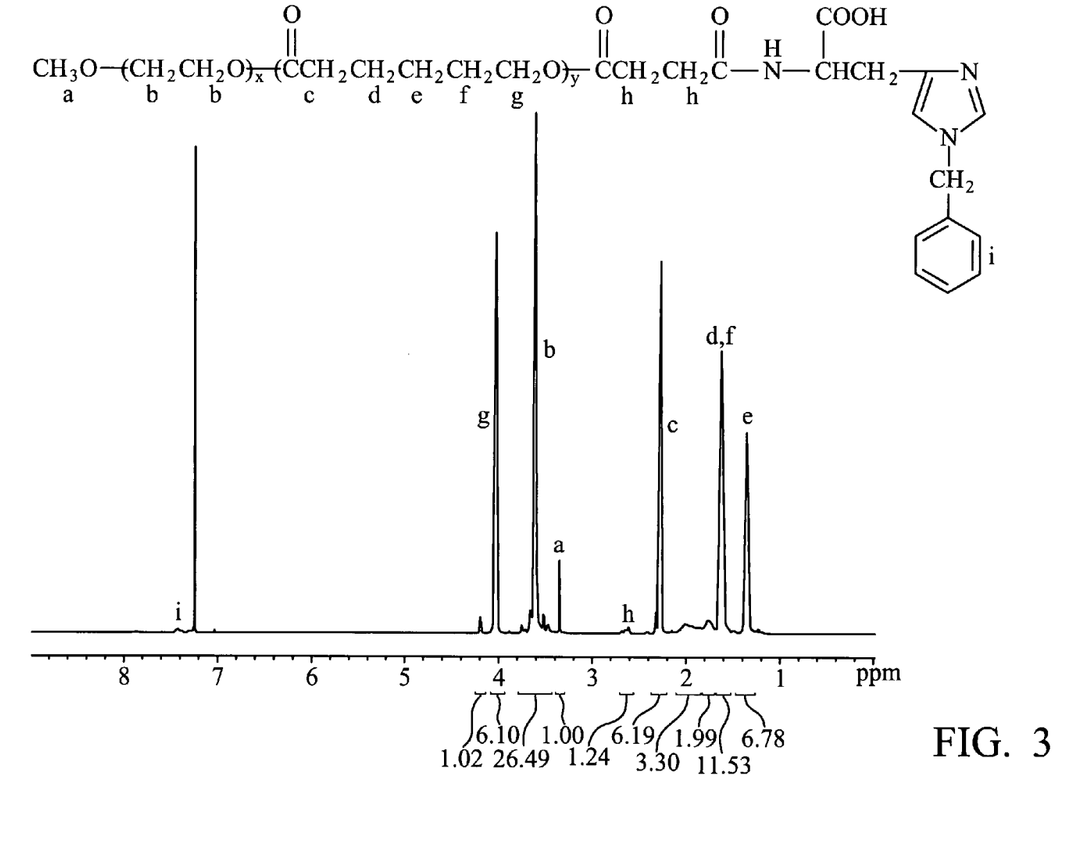
FIG. 3 shows $^1$H-NMR spectrum of PEG-PCL-benzyl histidine.

Synthesis of PEG-PCL-Benzyl Histidine
Coupling of PEG-PCL-SA and Benzyl Histidine 2 g PEG-PCL-SA copolymer, 0.1547 g N,N-dicyclohexyl carbodiimide (DCC) and 0.0863 g N-hydroxysuccinimide (NHS) were dissolved in 50 ml dichloromethane at 40° C. with mechanical stirring in a 250 ml flask. Another solution containing 0.368 g im-benzyl-L-histidine (His(Bzl)) dissolved in 100 ml methanol was prepared simultaneously. The His(Bzl)-contained solution was then added into the flask and reacted at 60° C. for 24 hours. The resulting solution was then cooled down to room temperature and filtered by 0.45 μm filter paper to remove the un-reaction material, His(Bzl). After removing dichloromethane, a modified copolymer, PEG-PCL-His(Bzl), was obtained. Its $^1$H-NMR is shown in FIG. 3.

The Critical Micelle Concentration (CMC) of Polymeric Micelles

The micelle CMC is measured by the method recited in Jeong et al., 1999. 0.4 mM DPH (1,6-diphenyl-1,3,5-hexatriene) water solution and copolymers with $2-2\times10^{-4}$ wt % were mixed. Absorption in 356 nm of the water solution was then measured by a UV-Vis spectrometer. Finally, the absorption was plotted in a diagram against logarithm of polymer concentrations. A turning point formed by two various slopes in the diagram is CMC.

Table 1 recited CMC values of the block copolymers is shown here.

TABLE 1

| Sample ID | Molecular weight of PEG (g/mole) | Molecular weight of PCL (g/mole) | CMC ($\times 10^{-2}$ wt %) |
|---|---|---|---|
| PEG-PCL-PC1 | 5000 | 1900 | 3.26 |
| PEG-PCL-PC2 | 5000 | 1100 | 17.92 |
| PEG-PCL-NS1 | 2000 | 1000 | 1.46 |
| PEG-PCL-NS2 | 2000 | 2000 | 4.47 |
| PEG-PCL-NS3 | 5000 | 2500 | 3.95 |
| PEG-PCL-NS4 | 5000 | 3700 | 7.76 |

Preparation of Micelles and Analysis of Sizes Thereof 10 mg polymer was dissolved in 1 ml THF to form a solution. The solution was gradually dropped into 30 ml deionized water by a 2.5 ml syringe and stirred. The solution was then placed in a dialysis membrane to dialyze for 24 hours to form a micelle solution. Finally, 3-5 ml micelle solution was placed in an acrylic cuvette to measure micelle sizes and their distribution by a photon correlation spectroscopy (Malvern Instrument Zetasizer Nano ZS), as shown in Table 2.

TABLE 2

| Sample ID | Molecular weight of PEG (g/mole) | Molecular weight of PCL (g/mole) | Hydrodynamic diameter (nm) |
|---|---|---|---|
| PEG-PCL-PC1 | 5000 | 1900 | 113.8 |
| PEG-PCL-PC2 | 5000 | 1100 | — |
| PEG-PCL-NS1 | 2000 | 1000 | 148.3 |
| PEG-PCL-NS2 | 2000 | 2000 | 34.7 |
| PEG-PCL-NS3 | 5000 | 2500 | 27.2 |
| PEG-PCL-NS4 | 5000 | 3700 | — |

In-Vitro Stealth Test

Figure 5:
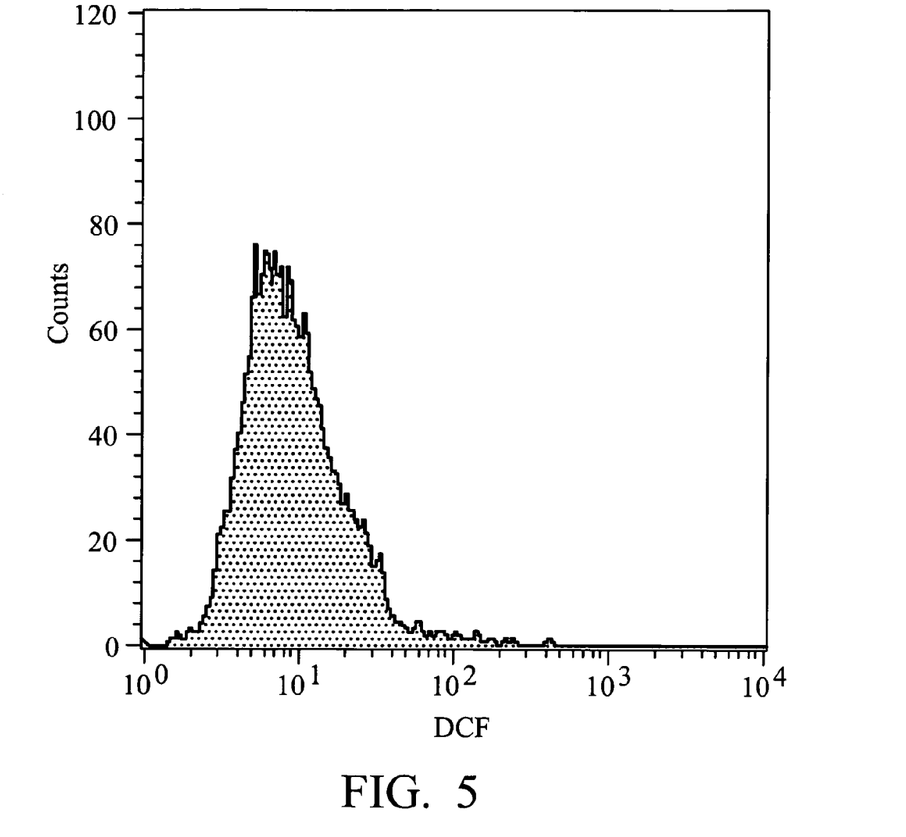
Figure 6:
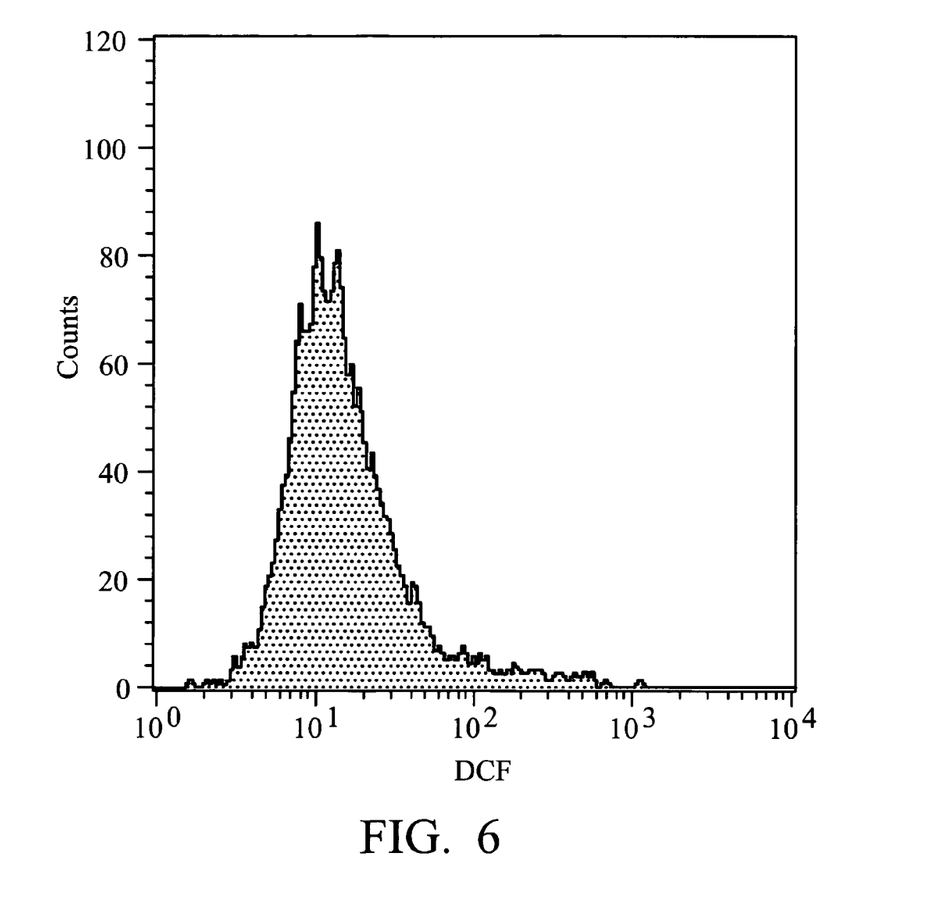

In blood, macrophage may be activated and produce reactive oxygen species after foreign substance is recognized thereby. Thus, the invisibility of micelles to macrophage can be determined by measuring the reactive oxygen species contents. 2',7'-dichlorodihydrofluorescein diacetate (DCFDA) was added into a microphage culture (RAW 264.7). A micelle solution having concentration above CMC was then added and cultivated for 24 hours. If micelles activate macrophage, DCFDA may be converted into fluorescent DCF (2',7'-Dichlorofluorescin) by reactive oxygen species and its fluorescence intensity is directly proportional to reactive oxygen species contents. Finally, the invisibility of micelles was obtained by measurement with a flow cytometer. The fluorescence intensity of DCF in various conditions is shown in FIGS. 4-6.

Figure 4:
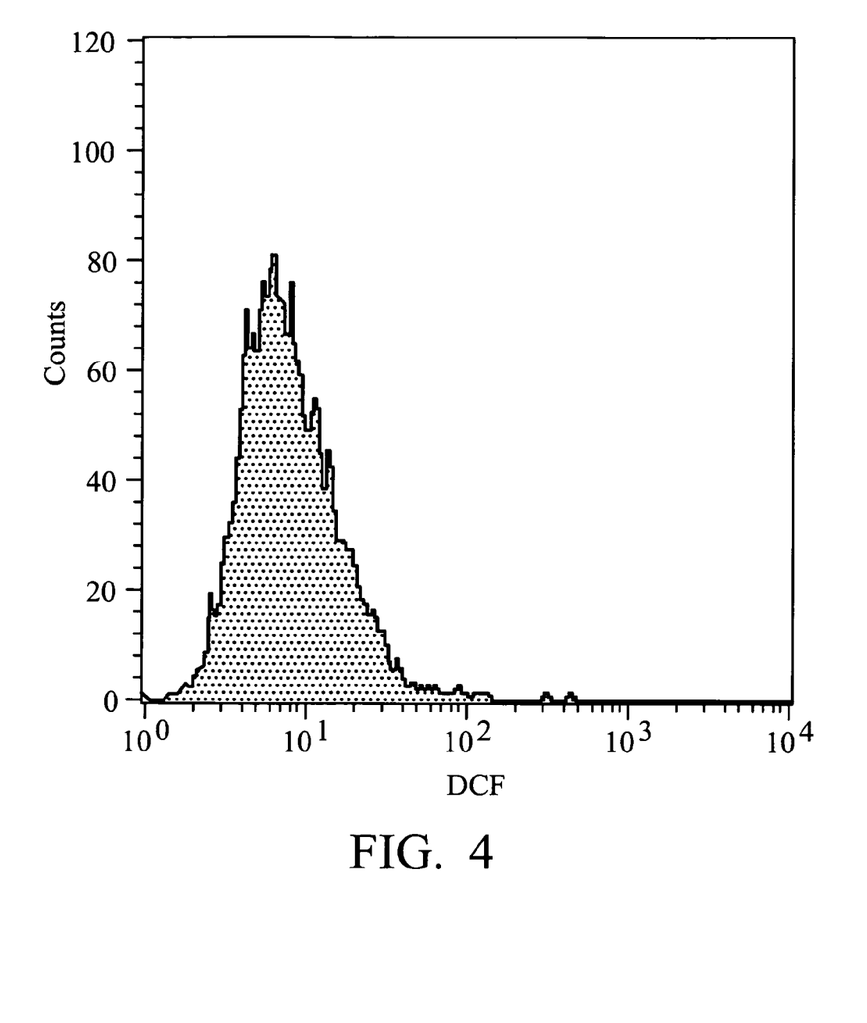
FIGS. 4-6 shows mean fluorescence intensity of DCF in various conditions.

FIG. 4 shows a mean fluorescence intensity of 9.39 without addition of micelles. FIG. 5 shows a mean fluorescence intensity of 10.8 with addition of micelles (PEG-PCL-PC2). FIG. 6 shows a mean fluorescence intensity of 20.13 with addition of 1 μm PMA for 24-hour activation. Due to the mean fluorescence intensity between (a) and (b) are similar, we can assert that the micelles are invisible.

Preparation of Polymeric Nano Particle 10 mg E50C19-PC was added into 1 mL dimethyl sulfoxide (DMSO) and stirred. After DMSO was removed by freeze-drying, 1 ml and 10% sucrose was added to hydrate. The freeze-dried solids were then dissolved to form a suspension. After ultra-sonicating for 10 min, polymer nano particles were formed. The particle size distribution of 120-150 nm was obtained by a laser particle size analyzer (Coulter N4 plus).

Preparation of Nano Carrier Containing Drugs

Camptothecin is a water-insoluble drug and has solubility of only 3 µg/ml. 1 mg camptothecin and 10 mg E50C19-PC were added into 1 ml dimethyl sulfoxide (DMSO) and stirred. After DMSO was removed by freeze-drying, 1 ml and 10% sucrose was added to hydrate. The freeze-dried solids were then dissolved to form a suspension. After ultra-sonicating for 10 min, polymer nano particles containing camptothecin were formed. The suspension was then filtered with a 0.45 µm filter to remove un-encapsulated camptothecin crystals. The particle size distribution of 130-190 nm was obtained by a laser particle size analyzer (Coulter N4 plus). The camptothecin concentration of 0.9 mg/ml in a micelle solution was measured by a HPLC. The solubility of camptothecin was increased to 300 times.

Hemolysis Test of Nano Carrier Containing Drugs

The toxicity of polymer micelles with and without camptothecin to erythrocyte was quantitatively analyzed by the ASTM F756 standard operation. The results shown in Table 3 inducate that the nano carriers are non-hymolytic.

TABLE 3

| Carrier type | Hemolytic index (%) | Hemolytic grade |
| --- | --- | --- |
| PEG-PCL-PC1 (placebo) | −0.07 | Non-hemolytic |
| PEG-PCL-PC1 nano carrier containing camptothecin | 0.44 | Non-hemolytic |

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A block copolymer comprising: a hydrophobic block, a hydrophilic block bonded to the hydrophobic block, and only one zwitterion, wherein the zwitterion, having one positive charge and one negative charge, is bonded to a terminal end of the hydrophobic block; the hydrophobic block is polycaprolactone (PCL), polyvalerolactone (PVL), poly(lactide-co-glycolide) (PLGA), polylactic acid (PLA), polybutyrolactone (PBL), polyglycolide, or polypropiolactone (PPL); and the hydrophilic block is polyethylene glycol (PEG), hyaluronic acid (HA) or poly-γ-glutamic acid (PGA).

2. The block copolymer as claimed in claim 1, wherein the hydrophobic block has a molecular weight of about 1000-30000.

3. The block copolymer as claimed in claim 1, wherein the zwitterion comprises phosphorylcholine (PC), sulfobetaine (NS), or an amino acid.

4. The block copolymer as claimed in claim 1, wherein the hydrophilic block has a molecular weight of about 550-20000.

5. The block copolymer as claimed in claim 1, wherein the copolymer is bio-degradable.

6. The block copolymer as claimed in claim 1, wherein the copolymer is bio-compatible.

7. A nano particle comprising one or more block copolymers as claimed in claim 1.

8. The nano particle as claimed in claim 7, wherein the nano particle has a hydrophobic interior and hydrophilic surface.

9. The nano particle as claimed in claim 7, wherein the nano particle has a diameter of about 20-1000 nm.

10. A nano carrier, comprising:
a nano particle as claimed in claim 7; and
an active substance encapsulated inside the particle.

11. The nano carrier as claimed in claim 10, wherein the active substance comprises water-insoluble drugs, growth factors, genes, or water-insoluble cosmetic substances.

12. The nano carrier as claimed in claim 10, wherein the active substance comprises camptothecin or derivatives thereof.

13. The nano carrier as claimed in claim 10, wherein the active substance comprises water-insoluble ingredients for skincare.

14. The nano carrier as claimed in claim 10, wherein the nano carrier is delivered by oral, transdermal administration, injection, or inhalation.

15. The block copolymer as claimed in claim 1, wherein the hydrophobic block is polycaprolactone (PCL), the hydrophilic block is polyethylene glycol (PEG), and the zwitterion is phosphorylcholine (PC), sulfobetaine (NS), or benzyl histidine.

16. The block copolymer as claimed in claim 15, wherein when the zwitterion is PC, the hydrophilic block has a molecular weight of 5000 and the hydrophobic block has a molecular weight of 1100-1900.

17. The block copolymer as claimed in claim 15, wherein when the zwitterion is NS, the hydrophilic block has a molecular weight of 2000-5000 and the hydrophobic block has a molecular weight of 1000-3700.

18. The block copolymer as claimed in claim 1, wherein the hydrophobic block is polycaprolactone, the hydrophilic block is polyethylene glycol, and the zwitterion is phosphorylcholine.

19. The block copolymer as claimed in claim 1, wherein the hydrophobic block is polylactic acid, the hydrophilic block is polyethylene glycol, and the zwitterion is phosphorylcholine.

* * * * *